(12) United States Patent  
Mukai

(10) Patent No.: US 7,079,250 B2  
(45) Date of Patent: Jul. 18, 2006

(54) STRUCTURE, STRUCTURE MANUFACTURING METHOD AND SENSOR USING THE SAME

(75) Inventor: Atsushi Mukai, Kanagawa (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 11/067,661

(22) Filed: Feb. 28, 2005

(65) Prior Publication Data

US 2005/0170494 A1    Aug. 4, 2005

Related U.S. Application Data

(62) Division of application No. 10/329,334, filed on Dec. 27, 2002.

(30) Foreign Application Priority Data

Jan. 8, 2002    (JP)    ............... P. 2002-001371

(51) Int. Cl.
 *G01N 21/55* (2006.01)
 *G01B 9/02* (2006.01)
(52) U.S. Cl. .............. 356/445; 257/226; 257/444; 356/450
(58) Field of Classification Search ............ 257/226, 257/444; 356/445, 450
See application file for complete search history.

(56) References Cited

U.S. PATENT DOCUMENTS

| 6,139,713 A | 10/2000 | Masuda et al. |
| 6,214,738 B1 | 4/2001 | Aiba et al. |
| 6,278,231 B1 | 8/2001 | Iwasaki et al. |
| 6,476,409 B1 | 11/2002 | Iwasaki et al. |
| 6,610,463 B1 | 8/2003 | Ohkura et al. |
| 6,737,668 B1 | 5/2004 | Den et al. |

FOREIGN PATENT DOCUMENTS

| JP | 2000-356587 A1 | 12/2000 |
| JP | 2001-9800 A1 | 1/2001 |
| JP | 2001-138300 A1 | 5/2001 |

OTHER PUBLICATIONS

"Solid State Physics" vol. 31, No. 5 1996.

*Primary Examiner*—Archene Turner
(74) *Attorney, Agent, or Firm*—Sughrue Mion, PLLC

(57) ABSTRACT

A plasmon resonance device 100 according to an example of a structure is characterized in that metallic particles 7 isolated from each other are formed in each of a plurality of pores 5 of anodic oxidized alumina 3. As a method of manufacturing the plasmon resonance device 100, a metal is coated on the anodic oxidized alumina 3 opening the pores 5 and a metal coated element provided on the opening surface of the pore in the anodic oxidized alumina 3 is removed. Consequently, metallic particles isolated from each other are formed in the respective independent pores. The plasmon resonance device 100 can be used as a sensor utilizing a localized plasmon resonance phenomenon.

11 Claims, 5 Drawing Sheets

STRUCTURE, STRUCTURE MANUFACTURING METHOD AND SENSOR USING THE SAME

This is a divisional of application Ser. No. 10/329,334 filed Dec. 27, 2002.

BACKGROUND OF THE INVENTION

1. Field of the Invention

The present invention relates to a structure mainly applying a localized plasmon resonance phenomenon, a method of manufacturing the structure and a sensor using the same, and more particularly to a technique for arranging metallic particles for inducing a plasmon resonance at a high density.

2. Description of the Related Art

Referring to a metal dot, such as formed by gold or silver with a smaller size being smaller than the wavelength of light, occurring a localized plasmon resonance is well known, and a device making use of said phenomenon is also known. Forming a metal colloid monolayer film is known as a method of forming such a device. For example JP-A2000-356587 has disclosed one of the utilizations of the properties. In this publication, metallic particles are fixed like a film on the surface of a substrate formed by an optional material such as a dielectric, a metal or a semiconductor and are thus used as a sensor unit, and light is irradiated on the sensor unit to measure the absorbance of the light transmitted through the metallic particles fixed to the substrate. Consequently, the refractive index of the medium in the vicinity of the surface of the metallic particles fixed to the substrate, for example, at a distance which is almost equal to the diameter of the metallic particle is obtained Thus, the detection of the adsorption and deposition of a substance onto the metallic particles in the sensor unit can be carried out.

In this case, the sensor unit is constituted by forming a metal colloid monolayer film by metallic particles having a diameter of approximately 10 to 20 nm on a substrate formed of glass. The metal colloid monolayer film is fabricated by immersing the substrate formed of glass in a 10% methanol solution of 3-aminopropyltriethoxysilane for 10 minutes, washing the substrate, and furthermore, immersing the substrate in a solution of metal colloid having a diameter of approximately 20 nm for two hours.

In the conventional sensor, however, a metal colloid monolayer film is formed and a large number of metallic particles are thus fixed onto the substrate. Therefore, the monolayer film can suitably be formed in a state in which the metallic particles are not condensed but isolated from each other. However, it is hard to carry out fabrication with the metallic particles having a uniform size and to regularly arrange the metallic particles.

More specifically, concerning the applicability to the sensing devices for detecting change made to the refractive index, the resonance condition being influenced by dispersion of the particle sizes or their shapes is the problem to be concerned as disclosed in the related art such as "Metal Nanoparticle, 89" by Daniel L. Feldheim and Colby A. Foss, Jr. Therefore, in case of such dispersion being not controllable, it brings about lowering the sensitivity because resonance-caused absorption or resonance wave length are also dispersed accordingly.

As an example, description will be given to the related art in which a thin poly(methyl methacrylate) (PMMA) film is deposited on the metallic particle 7 formed of gold fixed to the base material 11. In flus case, the absorbance of a resonance peak is increased and shifted toward the long wavelength side when the thickness of the thin PMMA film thus deposited is increased as shown in a result obtained by measuring the relationship between the wavelength and the absorbance for each thickness of the thin film in FIG. 4.

Further, when dispersion in the sizes or the shapes are occurring over a plurality of the sensing devices, it raises another problem, namely difficulty for determining whether the measured absorbance or resonance wave length are obtained from changes made in refractive index, or said dispersion in the sizes or the shapes, which might end up lowering its reliability of the sensing devices. The conventional choroids-used method, being known for forming metal particles, results in dispersion having ±6.6% even with its best mode as reported in the above mentioned "Metal Nanoparticle, 89". However, its range might be further enlarged through the conventional manufacturing process, such as to ±10% or so as reported in "Optical letters 25,6,372 (2000)" by Takayuki Okamoto. For the reasons mentioned above, a method for controlling dispersion of the particle sizes or their shapes has been expected.

SUMMARY OF THE INVENTION

The invention has been made in consideration of the circumstances and has an object to provide a structure in which metallic particles can be arranged regularly with an optional uniform size in an optional array, a method of manufacturing the structure and a sensor using the same, and furthermore, to enhance and stabilize a sensor sensitivity when the structure is to be used as the sensor and to provide a novel use of only a novel structure.

In order to attain the object, a first aspect of the invention is directed to a structure integrally comprising layer-like anodic oxidized alumina provided with a plurality of independent pores in an almost vertical direction with respect to a layer plane, and metallic particles filled in each of the independent pores of the anodic oxidized alumina and isolated from each other.

In the structure, the metallic particles are formed in the pore of the anodic oxidized alumina capable of comparatively freely controlling a pore size, a pore spacing and a pore depth, and the metallic particles can be fabricated with an optional uniform size and can be regularly arranged easily. Consequently, the metallic particles can be arranged at a higher density, and the sensor sensitivity of a device can be enhanced and the sensitivity can be stabilized when the structure is to be used as the sensor. Furthermore, it is possible to provide a novel use of only a novel structure.

A second aspect of the invention is directed to the structure, wherein the anode oxdized alumina is formed on a base material having at least aluminum on an uppermost layer.

In the structure, the anodic oxdized alumina is formed on the base material having at least aluminum on the uppermost layer. Consequently, a device can be held strongly and can be used as a transmission type sensor.

A third aspect of the invention is directed to a method of manufacturing a structure comprising the steps of coating layer-like anodic oxidized alumina provided with a plurality of independent pores in an almost vertical direction with respect to a layer plane with a metal from an opening surface side of the independent pore of the anodic oxidized alumina, and removing a coated layer of the metal formed on the opening surface of the independent pore of the anodic oxidized alumina, thereby forming metallic particles isolated from each other in each of the independent pores.

In the method of manufacturing the structure, the anodic oxidized alumina having the independent pores arranged at almost regular intervals in an almost vertical direction with respect to the layer plane is coated with the metal. Consequently, the respective pores can be filled with the metal. Then, the metal coated film formed on the opening surface of the independent pore of the anodic oxidized alumina is removed so that the metals coated and filled in the independent pores remain in an isolation state from each other. As a result, the metallic particles which are independent of each other are arranged at regular intervals and a high density.

A fourth aspect of the invention is directed to a sensor in which light is irradiated on the structure according to the first or second aspect of the invention, and an absorbance of light reflected from or transmitted through metallic particles in the structure is measured to detect a refractive index of a medium in the vicinity of the metallic particles fixed to a substrate.

In the sensor, the light is irradiated on the structure and the absorbance of the light reflected from or transmitted through the metallic particles in the structure is measured so that the refractive index of the medium in the vicinity of the metallic particles is measured Consequently, it is possible to detect the refractive index of the medium in the vicinity of the surface of the metallic particles fixed to the substrate. Thus, it is possible to detect the adsorption and deposition of a substance to the metallic particles in the structure.

DESCRIPTION OF THE PREFERRED EMBODIMENTS

A preferred embodiment of a structure, a method of manufacturing the structure and a sensor using the same according to the invention win he described below in detail with reference to the drawings.

Figure 1:
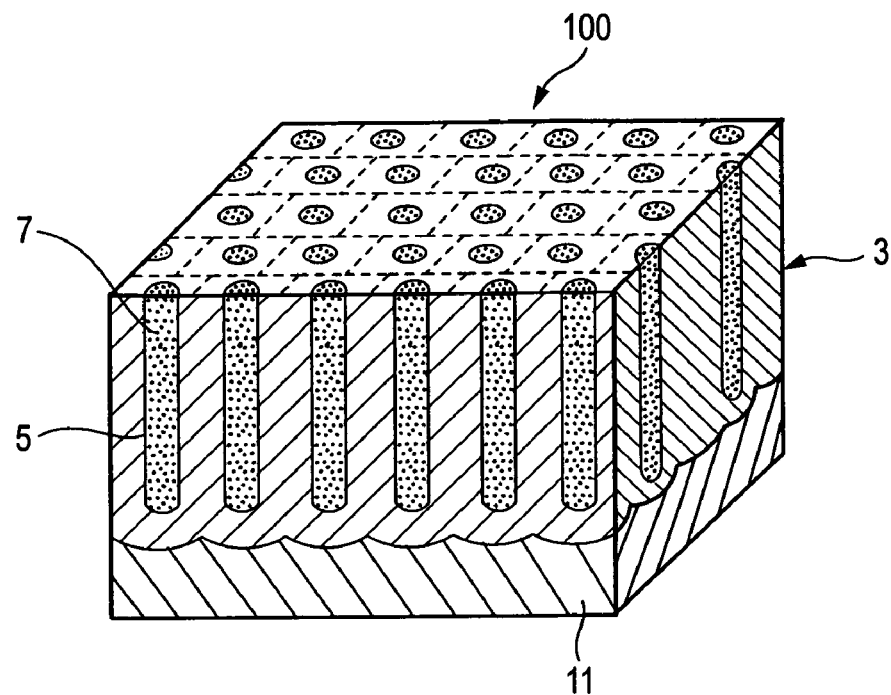
FIG. 1 is a perspective view showing a main part according to a first embodiment of a structure in accordance with the invention.
Figure 2:
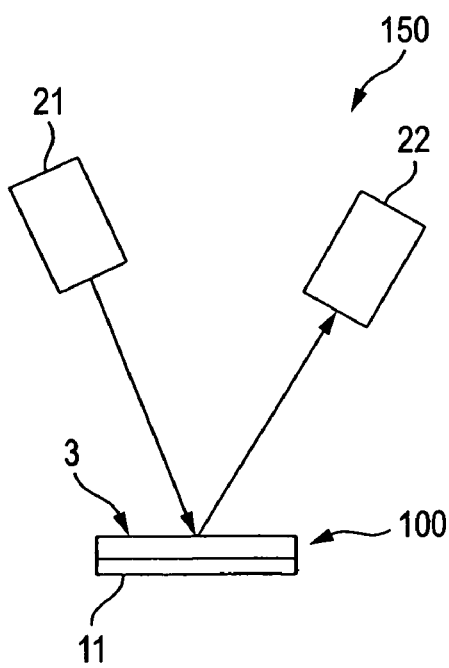
FIG. 2 is a view illustrating a state in which a measurement is carried out by using the structure shown in FIG. 1 as a sensor.

FIG. 1 is a perspective view showing a main part according to a first embodiment of the structure in accordance with the invention and FIG. 2 is a view illustrating a state in which a measurement is carried out by using the structure as the sensor.

In a plasmon resonance device 100 according to an example of the structure in accordance with the invention, a metallic particle 7 is filled in each of a plurality of pores 5 of anodic oxide alumina 3 formed like a layer and a metallic particle dispersing element having the metallic particles isolated from each other is thus formed.

A method of manufacturing the anodic oxidized alumina 3 will be described below and the anodic oxidized alumina 3 has the pores 5 formed at almost regular intervals in an almost vertical direction with respect to a layer plane. In other words, the pores are provided regularly in the layer. For this reason, the metallic particles 7 filled in the pore 5 are isolated from each other and are provided regularly as a whole. Consequently, the plasmon resonance device 100 having a dot size of several hundreds nm or less can easily be fabricated.

The anodic oxidized alumina 3 is a porous oxide film formed on an aluminum surface by anodic oxidizing aluminum in an acid electrolyte. The anodic oxidized alumina 3 to be a porous material has the greatest feature of a honeycomb structure in which the pores are formed in parallel at almost regular intervals in an almost vertical direction with respect to the layer plane. In addition, the anodic oxidized alumina 3 has a feature in that a pore size, a pore spacing and a pore depth can be controlled comparatively freely, which is not owned by other materials (Hideki Masuda, Solid State Physics, Vol. 31 No. 5 1996).

In the embodiment, gold (Au) is used as the metallic particle 7. Consequently, the metallic particle 7 is formed of gold which is a good conductor and has a great malleability and ductility, and can be thereby deposited well at a low temperature. In addition, since the metallic particle 7 has a corrosion resistance, the stable characteristic of a sensor to be described below can be obtained for utilization as the sensor. Moreover, the plasmon resonance device 100 can easily be handled during and after the manufacture of the plasmon resonance device 100. While description will be given by talking, as an example, the case in which the gold is used for the metallic particle 7, silver can also be used suitably, for example. In that case, it is possible to more increase a sensor sensitivity when the plasmon resonance device 100 is used as the sensor.

In the embodiment, moreover, the metallic particle 7 is filled to reach the bottom portion of the pore 5 and an unfilled space is not formed in the pore 5. By such a structure, the adhesion force of the pore 5 and the metallic particle 7 is increased so that the fixing strength of the metallic particle 7 is increased. Moreover, the depth of the pore 5 is almost uniform. By such a dense filling structure that the unfilled space is not generated, therefore, the amount of the metallic particles 7 to be filled in each of the pores 5 becomes uniform. Thus, the stability of the sensor sensitivity can be enhanced when the metallic particle 7 is used as a detection substance.

FIG. 2 is a view showing a conceptual structure in the case in which the structure is used as a sensor utilizing a plasmon resonance phenomenon. A sensor 150 is constituted to have the plasmon resonance device 100, a light source 21 such as a laser from which a light beam is incident on the plasmon resonance device 100, and a spectrophotometer 22 for measuring the absorbing spectrum of light reflected from the plasmon resonance device 100 to obtain an absorbance. According to the sensor 150 having the structure described above, when a substance is adsorbed or deposited on the metallic particle 7 of the plasmon resonance device 100, the absorbance of the light reflected from the plasmon resonance device 100 is changed so that it is possible to detect the adsorption or deposition of the substance on the metallic particle 7.

More specifically, the light beam is irradiated on the plasmon resonance device 100 from the light source 21 and the absorbing spectrum of the light reflected from the plasmon resonance device 100 is measured by the spectrophotometer 22 to obtain an absorbance for each wavelength. Consequently, it is possible to detect a change in a refractive index of a medium in the vicinity of the surface of the metallic particle 7. Consequently, it is possible to detect the adsorption or deposition of the substance on the metallic particle 7. Moreover, since the device is formed on a base material, the device itself is held strongly.

Figure 3:
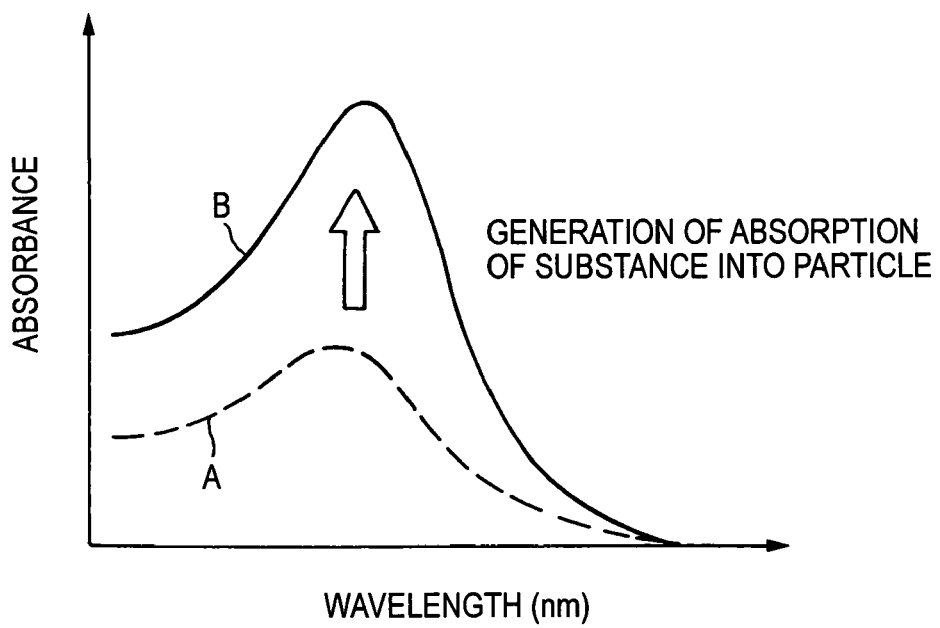
FIG. 3 is a graph showing the relationship between an absorbance and a wavelength for the reflected light of a plasmon resonance device.
Figure 4:
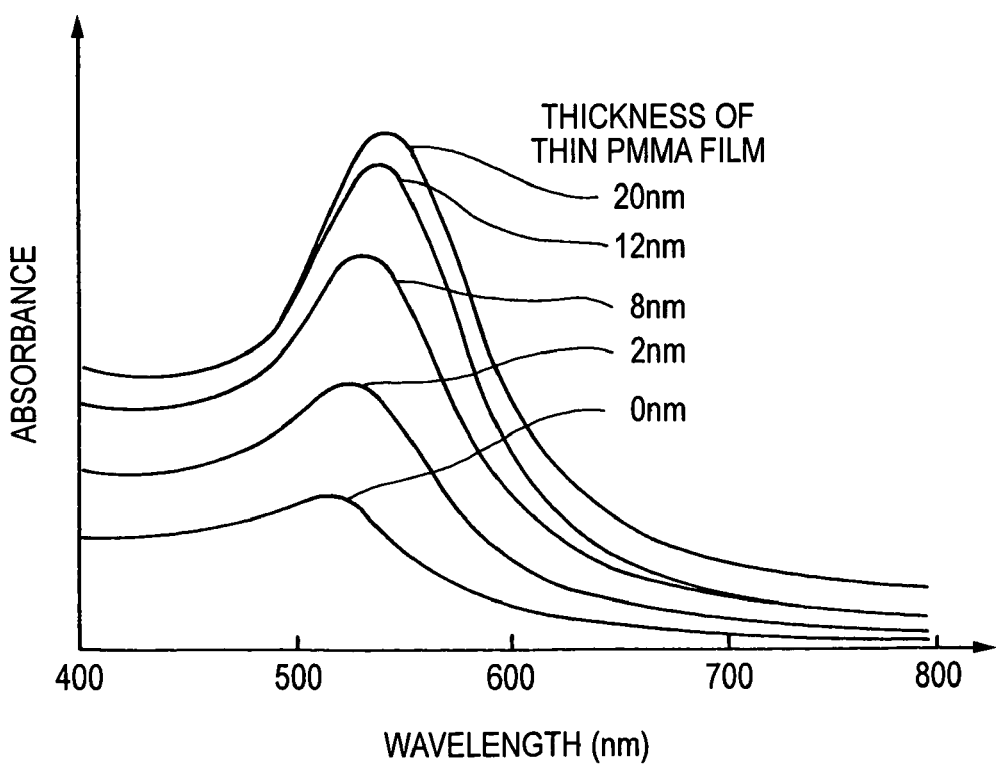
FIG. 4 is a graph showing a result obtained by measuring the relationship between a wavelength of transmitted light and an absorbance for each thickness of a thin film in the case in which a thin poly(methyl methacrylate) film is deposited on metallic particles fixed to a base material.

FIG. 3 shows, in a graph, the relationship between an absorbance and a wavelength for the reflected light of the plasmon resonance device. The absorbing spectrum of the light transmitted through and reflected by the metallic particle 7 is measured by the spectrophotometer 22 to obtain an absorbance for each wavelength of the reflected light. Consequently, there is obtained a distribution in which a resonance peak appears in a predetermined wavelength corresponding to the relationship between the dielectric constant of the metallic particle and that of a surrounding medium by a localized plasmon phenomenon (A in FIG. 3). As compared with the case in which a substance is neither adsorbed nor deposited on the metallic particle 7 and a medium surrounding the metallic particle 7 is air, the absorbance of the resonance peak is more increased and shifted toward the long wavelength side in the case in which a substance having a greater refractive index than that of the air is adsorbed or deposited on the metallic particle 7 and functions as the medium surrounding the metallic particle 7 (B in FIG. 3).

In the embodiment, accordingly, it is possible to detect the refractive index of a medium in the vicinity of the surface of the metallic particle 7, for example, at a distance which is almost equal to the diameter of the metallic particle 7 (the diameter of the pore 5) by measuring the absorbance of the reflected light emitted from the plasmon resonance device 100 to be the structure. As a result, it is possible to detect the adsorption or deposition of the substance on the metallic particle 7 fixed to a base material 11 of the plasmon resonance device 100.

In the case in which the plasmon resonance device 100 is provided in a liquid, moreover, the refractive index of the liquid can also be measured. Since it is sufficient that the metallic particle 7 is fixed to the base material 11, the plasmon resonance device 100 can be provided in a narrow place without requiring a prism.

The sensor 150 according to the invention has such a structure that the arrangement density of the metallic particle 7 in the plasmon resonance device 100 is increased. Therefore, it is possible to carry out sensing with a higher sensitivity by means of a sensor comprising a colloid monolayer film described in JP-A-2000-356587, for example.

Next, description will be given to a method of manufacturing the plasmon resonance device as an example of the structure.

Figure 5:
FIGS. 5(a), 5(b), 5(c) and 5(d) show the views showing a procedure for manufacturing the plasmon resonance device illustrated in FIG. 1.
Figure 5:
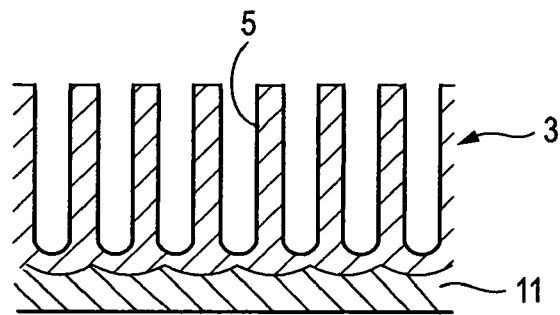
Figure 5:
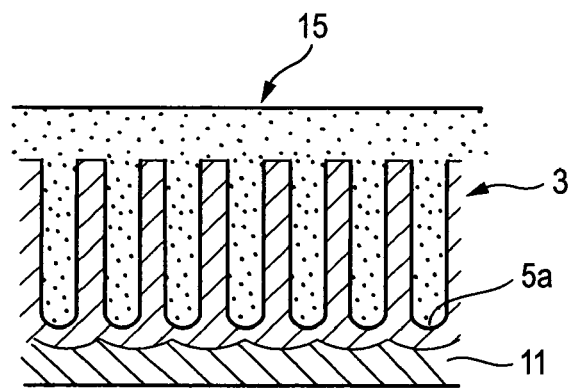
Figure 5:
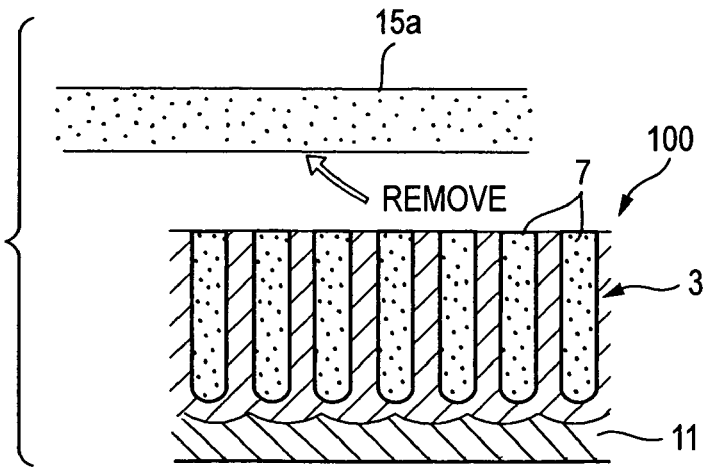

FIG. 5 shows a procedure for manufacturing the plasmon resonance device illustrated in FIG. 1.

First of all, as shown in FIG. 5(a), the base material 11 for fabricating anodic oxide alumina having a pore for forming a metallic particle is prepared. A bulk material containing aluminum as a principal component is used for the base material 11. In addition, an aluminum film may be formed on a glass substrate, for example, and a base material having at least aluminum on an uppermost layer is enough.

As shown in FIG. 5(b), next, the anodic oxidized alumina 3 having the pore 5 is formed on the base material 11. There are some methods of forming the anodic oxidized alumina 3. Basically, there is used a forming method of simultaneously progressing the formation of an oxide layer and the dissolution of the generated oxide layer when anodic oxidizing the aluminum of the base material 11 in an acid electrolyte. According to this method, very small pits are randomly generated by an acid dissolving action on the surface of the oxide film formed on the surface of the aluminum at an early stage of the start of anodic oxidation. With the progress of the anodic oxidation, some of the pits grow preferentially and are arranged at almost regular intervals. In a portion of the oxide film in which a hole is once formed, a higher electric field that in other portions is applied. Therefore, the dissolution in that portion is more promoted. As a result, the anodic oxidized layer is provided with a portion which is selectively dissolved with the growth and thus becomes the hole and a portion of a wall which is not dissolved but remains to surround the hole.

The anodic oxidized alumina 3 thus obtained is provided with the pores 5 arranged regularly on one of the surfaces of the base material 11 formed of aluminum. The pore 5 becomes a cylindrical space having an almost identical sectional shape in an almost vertical direction with respect to the layer plane of the anodic oxidized alumina 3 thus formed, and a bottom portion is closed.

As shown in FIG. 5(c), next, the gold is coated by deposition or sputtering on the opening surface side of the pore 5 in the formed anodic oxidized alumina 3. Thus, a coated element 15 is formed. In the embodiment, the gold grows from a bottom portion 5a of the pore 5 and is thereby filled in all the spaces of the pores 5.

As shown in FIG. 5(d), subsequently, only a coated element 15a stuck to the surface on the opening side of the pore 5 in the anodic oxidized alumina 3 is removed leaving the gold filled in the pore 5. Consequently, the gold filled in the pore 5 is isolated so that the metallic particle 7 arranged regularly is obtained. The gold is effectively removed from the surface of the anodic oxidized alumina 3 by rubbing using a swab and may be removed by polishing using a file.

Repeating the above process, it is also possible to control the dispersion of fill amount by filling the gold into the pore to the surface of alumina so as to control the size to the same level of the diameter's dispersion of the alumina pore such as the range of ±3% or smaller.

Referring to the control of the pore 5, a method of forming a pore formation starting point has been disclosed in JP-A-2001-9800 and JP-A-2001-138300. More specifically, a pore formation starting point is formed in a desirable position in a portion containing aluminum to be a processed substance as a principal component. After the step, the processed substance is anodic oxidized so that a pore can be formed in a desirable position and the arrangement, spacing, position and direction of the pores of a nanostructure can be controlled. Examples of the method of forming a pore formation starting point include a method of irradiating a focusing ion beam. In the method using a focusing ion beam, it is possible to control the concave shape and composition of a pore starting point by controlling focusing ion beam irradiating conditions such as the irradiation amount of the focusing ion beam, a beam diameter and an ion irradiation energy. Consequently, it is possible to control the final pore size of a nanohole.

Moreover, examples of a method of particularly increasing the density of the array of the pore 5 includes a method using oxalic acid, for example. More specifically, the oxalic acid is used for an electrolyte and anodic oxidizing treatment is carried out under a constant voltage condition of approximately 40 V so that the regulation of a pore at a high density progresses. The regulation of a pore array progresses with an anodic oxidation time and the anodic oxidizing treatment is carried out for a long time so that the pore can be arranged almost ideally. Consequently, the pore array of anodic oxidized alumina thus obtained has an exceptionally high regularity as a structure to be formed naturally.

According to the plasmon resonance device 100 in accordance with the embodiment, thus, a metal is filled in each of the pores 5 formed independently in the anodic oxidized alumina 3 which can control a pore size, a pore spacing and a pore depth comparatively freely so that the metallic particle 7 can be fabricated with an optional uniform size and can be arranged regularly. As a result, its diameter's dispersion of the alumina pore can be lowered to the range of ±3% or smaller so that signal fluctuation due to the positioning of the devices can be lowered and device dependency can be also lowered in-between.

Next, a variant of the structure according to the embodiment will be described.

Figure 6:
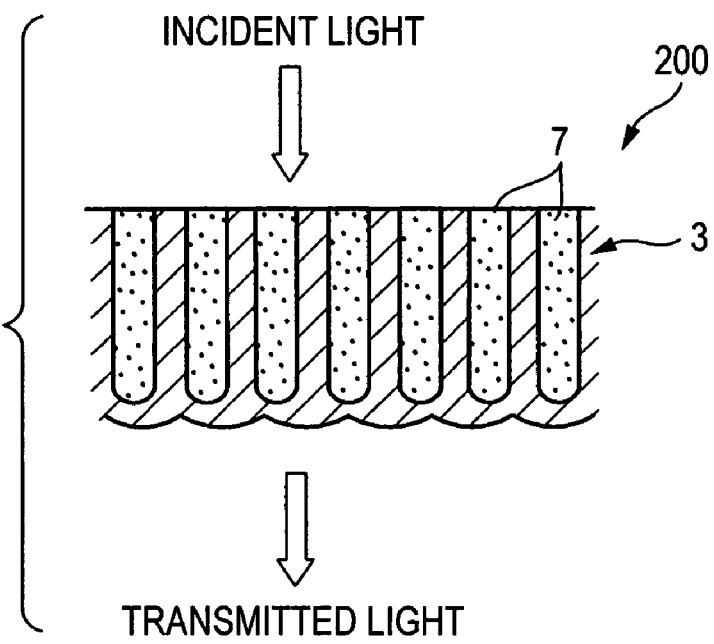
FIG. 6 is a sectional view showing the main part of a plasmon resonance device according to a variant of the first embodiment.

FIG. 6 is a sectional view showing the main part of the structure according to the variant.

In the variant, the aluminum to be the base material 11 is removed from the structure (plasmon resonance device) 100 in which the metallic particle 7 is filled in the pore 5 of the anodic oxidized alumina 3 shown in FIG. 1. The base material 11 is removed by using a method of removing the base material 11 by etching, for example. In this case, accordingly, only a thin anodic oxidized alumina 3 layer remains and is set to be a plasmon resonance device 200 so that a flexibly deformable device can be obtained. Moreover, a transmission method for measuring transmitted light as well as the reflection type can also be employed for the measurement of an absorbance. Thus, it is possible to enhance the degree of freedom of the use of the plasmon resonance device 200.

Figure 7:
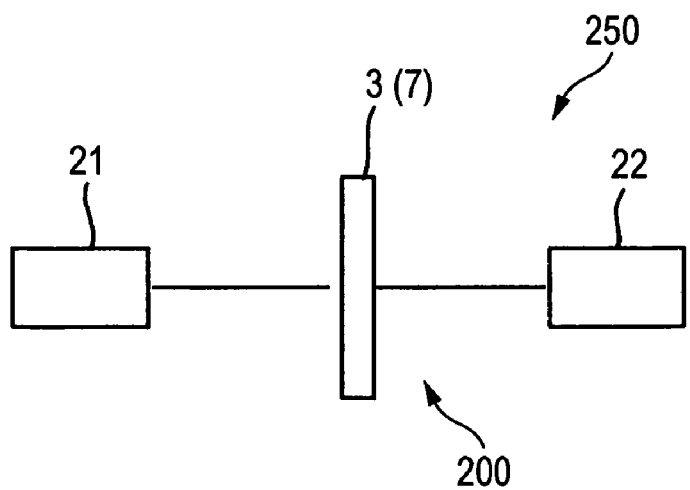
FIG. 7 is a view showing a conceptual structure in the case in which the plasmon resonance device illustrated in FIG. 6 is used as a sensor utilizing a plasmon resonance phenomenon.

FIG. 7 is a view showing a conceptional structure in the case in which the plasmon resonance device according to the variant is used as a sensor utilizing a plasmon resonance phenomenon. A sensor 250 is constituted to have the plasmon resonance device 200, a light source 21 such as a laser from which a light beam is incident on the plasmon resonance device 200, and a spectrophotometer 22 for measuring the absorbing spectrum of light transmitted through the plasmon resonance device 200 to obtain an absorbance.

According to the sensor 250 having the structure described above, when light having a transparent wavelength for the plasmon resonance device 200 is incident on the plasmon resonance device 200, the incident light passing through a substrate is incident on the metallic particle 7 and the incident light transmitted through the metallic particle 7 is emitted as transmitted light forward in an optical path. When the light is incident on the metallic particle 7 such as gold or silver, scattering light or absorption is increased at a certain wavelength by the localized plasmon resonance phenomenon so that a resonance peak appears. As shown in FIG. 7, a light beam is irradiated from the light source 21 and the absorbing spectrum of the light transmitted from the plasmon resonance device 200 is measured by a spectrophotometer 22 to obtain an absorbance for each wavelength. Consequently, a change in the refractive index of a medium in the vicinity of the surface of the metallic particle 7 is detected. Thus, it is possible to detect the adsorption or deposition of a substance on the metallic particle 7 in the same manner as described above.

Next, a second embodiment of the structure according to the invention will be described.

Figure 8:
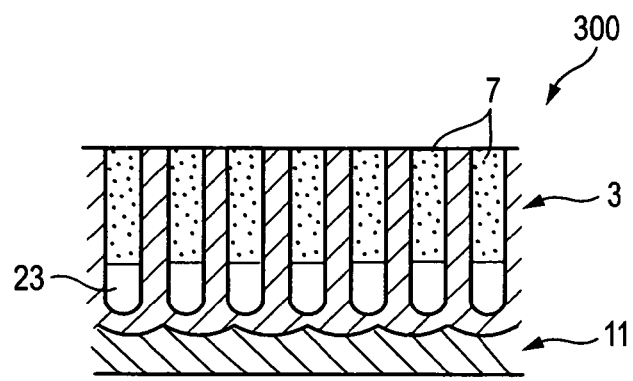
FIG. 8 is a sectional view showing the structure of a plasmon resonance device Structure) according to a second embodiment.

FIG. 8 is a sectional view showing the construction of a structure plasmon resonance device (structure) according to the embodiment. The same members as those shown in FIG. 1 have the same reference numerals and repetitive description will be omitted.

A plasmon resonance device 300 according to the embodiment has a hollow portion 23 which is not filled with a metal (gold) in the bottom portion of a pore 5. Other structures are the same as those of the plasmon resonance device 100 according to the first embodiment.

Also in the plasmon resonance device 300 thus constituted, a light beam is irradiated on the plasmon resonance device 300 from a light source and the absorbing spectrum of light reflected from or transmitted through the plasmon resonance device 300 is measured by a spectrophotometer to obtain an absorbance so that a change in the refractive index of a medium in the vicinity of the surface of a metallic particle 7 can be detected as shown in FIGS. 2 and 7. Consequently, it is possible to detect the adsorption or deposition of a substance on the metallic particle 7. Silver may be used for the metallic particle 7 in place of the gold and aluminum to be a base material 11 may be removed.

Next, a procedure for manufacturing the plasmon resonance device will be described.

Figure 9:
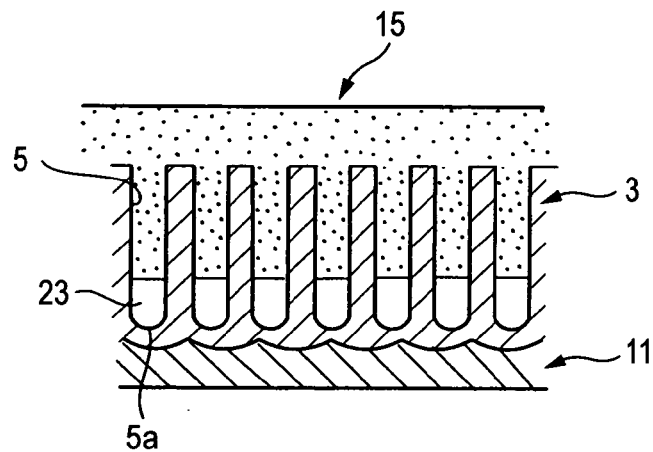
FIGS. 9(a) and 9(b) show the views illustrating a procedure for manufacturing the plasmon resonance device according to the second embodiment, (a) being a sectional view showing a state in which a metal is deposited or sputtered on anodic oxidized alumina shown in FIG. 5 and (b) being a sectional view showing a state in which a deposition provided on the upper surface of the anodic oxidized alumina is removed.
Figure 9:
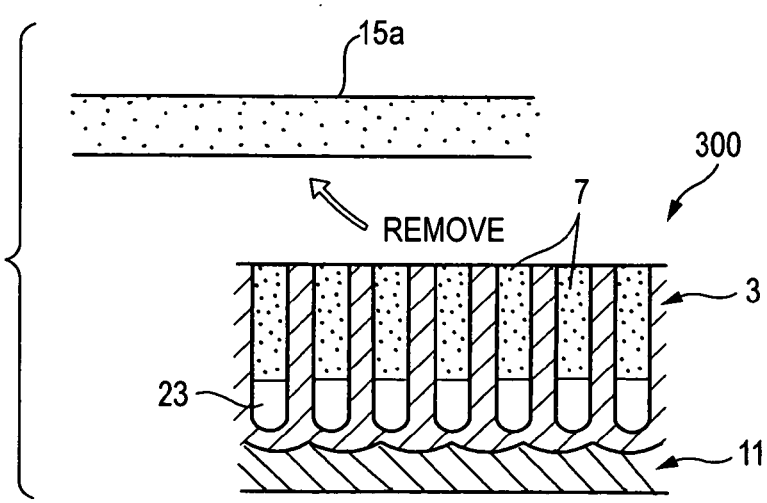

FIG. 9 is a view illustrating the procedure for manufacturing the plasmon resonance device according to the embodiment, (a) being a sectional view showing a state in which a metal is deposited or sputtered on anodic oxidized alumina illustrated in FIG. 8 and (b) being a sectional view showing a state in which a coated element is removed from the upper surface of the anodic oxidized alumina.

Anodic oxidized alumina 3 shown in FIG. 9(a) which is obtained in the same manner as in the first embodiment is formed with the pores 5 arranged with a high regulation on one of the surfaces of the base material 11 formed of aluminum. Gold is deposited or sputtered on the opening surface side of the pore 5 in the anodic oxidized alumina 3 to form a coated element 15. In the embodiment, the gold does not reach a bottom portion 5a of the pore 5 but grows in the middle of the pore 5, and a hollow portion 23 is formed in the vicinity of the bottom portion 5a of the pore 5.

As shown in FIG. 9(b), subsequently, only a coated element 15a stuck to the surface of the anodic oxidized alumina 3 is removed leaving the gold filled in the pore 5. Consequently, the gold filled in the pore 5 is isolated so that the metallic particle 7 arranged with a high regularity is obtained The gold is effectively removed from the surface of the anodic oxidized alumina 3 by rubbing using a swab and may be removed by polishing using a file in the same manner as described above.

According to the plasmon resonance device as an example of the structure according to each of the embodiments described above, the metallic particle 7 is formed in the pore 5 of the anodic oxidized alumina 3 which can control a pore size, a pore spacing and a pore depth comparatively freely. Consequently, the metallic particle 7 can be fabricated with an optional uniform size and can be arranged regularly. As a result, the metallic particle 7 can be arranged at a higher density and a sensor sensitivity can be more increased so that the sensitivity can be stabilized Moreover, the structure according to the invention can be utilized as the plasmon resonance sensor, and furthermore, can be suitably applied to the following uses, for example.

First of all, the structure can be used as a test tool utilizing the fact that an antibody is attached to a metallic particle and the wavelength of light to be reflected is varied depending on the degree of binding of an antigen and the antibody. More specifically, the adsorption or deposition of a substance on the metallic particle such as gold or silver is detected. In addition, since the optical properties of the structure are also changed depending on the degree of the binding to the antibody stuck to the metallic particles the change is detected so that the antigen can be detected.

Secondly, a dye such as a pigment, for example, red, blue or green is stuck to metallic particles arranged regularly and they can also be used as display members for displaying a static image or a dynamic image. More specifically, the dye such as red, blue or green is stuck to the metallic particles of the structure and a laser beam is scanned and exposed so that an optional image can be displayed by the light emission of the dye.

In addition to the examples of the uses of the structure, the structure can be suitably used for a novel application object without departing from the scope of the invention. Consequently, it is possible to provide a novel use of only a novel structure.

As described above in detail, according to the structure of the invention, the metallic particles are filled in the pore of the anodic oxidized alumina capable of comparatively freely controlling a pore size, a pore spacing and a pore depth, and the metallic particles can be fabricated with an optional uniform size and can be regularly arranged. The sensor sensitivity of a device can be enhanced and stabilized when such a structure is to be used as the sensor. Furthermore, it is possible to provide a novel use of only a novel structure.

According to the method of manufacturing the structure in accordance with the invention, moreover, the metal is deposited on the anodic oxidized alumina having the independent pores arranged at almost regular intervals in an almost vertical direction with respect to the layer plane so that the coating is carried out with the respective pores filed with the metal, and the metal provided on the anodic oxidized alumina is removed so that only the metal in the pores can be caused to remain in an isolation state from each other. As a result, the metallic particles which are independent of each other can be arranged at regular intervals and a high density.

According to the sensor in accordance with the invention, moreover, the absorbance of the reflected light or transmitted light emitted from the structure is measured. Consequently, it is possible to detect the refractive index of the medium in the vicinity of the surface of the metallic particle with a high sensitivity. As a result, it is possible to detect the adsorption or deposition of a substance on the metallic particle fixed to the substrate of the structure with high precision.

What is claimed is:

1. A plasmon resonance device comprising:
   a layer-like anodic oxidized alumina comprising a plurality of independent pores; and
   metallic particles filled in each of the independent pores of the anodic oxidized alumina, wherein:
   each of the independent pores are isolated from each other;
   each of the independent pores extend orthogonally to a layer plane; and
   the plasmon resonance device is operable to reflect and transmit light so that an absorption or deposition of a substance on the metallic particles is measurable.

2. The device according to claim 1, wherein the anodic oxidized alumina is formed on a base material having at least aluminum on an uppermost layer.

3. The device according to claim 1, wherein the layer-like anodic oxidized alumina forms the entire sides and bottom of each of the plurality of independent pores.

4. The device according to claim 1, wherein the metallic particles are gold.

5. The device according to claim 1, wherein the metallic particles are silver.

6. The device according to claim 1, wherein the metallic particles completely fill each of the independent pores.

7. The device according to claim 1, wherein: the metallic particles fill an upper portion of each of the independent pores; and a lower portion of each of the independent pores is hollow.

8. The device according to claim 1, wherein the diameter dispersion of the independent pores is in the range of ±3% or smaller.

9. The device according to claim 1, wherein a top surface of the layer-like anodic oxidized alumina is planar, and has an alternating surface structure of anodic oxidized alumina and the metallic particles filled in the independent pores.

10. The device according to claim 1, wherein the device is flexible.

11. The device according to claim 1, wherein the layer-like anodic oxidized alumina forms both the top and bottom surface of the plasmon resonance device.

* * * * *